United States Patent [19]

Shu et al.

[11] Patent Number: 4,731,331
[45] Date of Patent: Mar. 15, 1988

[54] RATE METHOD FOR THE DETERMINATION OF INORGANIC PHOSPHORUS

[75] Inventors: Frank R. Shu, LaHabra Heights; James H. Francis, Brea, both of Calif.

[73] Assignee: Beckman Instruments, Inc., Fullerton, Calif.

[21] Appl. No.: 824,689

[22] PCT Filed: Apr. 9, 1984

[86] PCT No.: PCT/US84/00549
§ 371 Date: Jul. 17, 1984
§ 102(e) Date: Jul. 17, 1984

[87] PCT Pub. No.: WO85/04721
PCT Pub. Date: Oct. 24, 1985

[51] Int. Cl.$^4$ ................. G01N 21/78; G01N 33/52
[52] U.S. Cl. ................................ 436/34; 436/103; 436/105; 436/164
[58] Field of Search ............... 436/8, 103, 105, 34, 436/164

[56] References Cited

U.S. PATENT DOCUMENTS

| | | | |
|---|---|---|---|
| 3,425,805 | 2/1969 | Grobin | 436/103 |
| 3,547,586 | 12/1970 | Denney et al. | 436/105 |
| 3,795,484 | 3/1974 | Daly et al. | 436/105 X |
| 3,853,469 | 12/1974 | Morin et al. | 436/105 |
| 3,874,853 | 4/1975 | Byrnes | 436/105 |
| 3,953,359 | 4/1976 | Gindler | 436/105 |
| 4,009,004 | 2/1977 | Hutchinson | 436/105 |
| 4,220,451 | 9/1980 | Stefanchik | 436/105 |

FOREIGN PATENT DOCUMENTS 0100187 2/1984 European Pat. Off. .

OTHER PUBLICATIONS

Ho et al., Anal. Biochem., vol. 60, pp. 413–416, 1974.
Allin et al, Biochim. Biophys. Acta, vol. 127, No. 1, pp. 521–523, 1966.
LeBel et al., Anal. Biochem., vol. 85, pp. 86–89, 1978.
Leigh et al., Anal. Biochem., vol. 106, pp. 279–284, 1980.
McCoy et al, Chemical Abstracts, vol. 97, Abstract No. 97:3105b, 1982.
Daly et al., Clin. Chem., vol. 18, No. 3, pp. 263–265, 1972.
Woods et al., Ind. Eng. Chem., vol. 13, No. 11, pp. 760–764, 1941.
Lundgren, Anal. Chem., vol. 32, No. 7, pp. 824–828, 1960.

Primary Examiner—Michael S. Marcus
Assistant Examiner—Robert J. Hill, Jr.
Attorney, Agent, or Firm—W. H. May; Arnold Grant

[57] ABSTRACT

A reagent of the type comprising an acid, a molybdate salt, a non-ionic surfactant, and polyvinylpyrrolidone (PVP). The reagent is characterized in that it further comprises an enhancing amount of at least one sugar alcohol. Also, a method for assaying inorganic phosphorus of the type which comprises mixing a sample of biological fluid with a reagent and measuring the absorbance of the resulting solution. The method is characterized in that the above reagent is employed therein. The method can further be characterized in that the measurement can be made via a rate technique.

14 Claims, No Drawings

RATE METHOD FOR THE DETERMINATION OF INORGANIC PHOSPHORUS

BACKGROUND OF THE INVENTION

1. Field of the Invention

The instant invention pertains to a method for assaying inorganic phosphorus and to a reagent for use therein.

2. Description of the Prior Art

The use of molybdate in the determination of inorganic phosphorus was first suggested by Woods et al (1). Woods et al found that under suitable conditions molybdates react with phosphates to form heteropoly compounds such as ammonium phosphomolybdate. These compounds absorb in the ultraviolet range or can be reduced, using any of a wide range of reducing agents under conditions which do not reduce the excess molybdate present, to form molybdenum blue which can be measured at wavelengths above 600 nm.

Until now, all methods for phosphorus determination on whole serum (i.e., serum which has not been deproteinized) have been performed by an end point technique (2-7). In the end point technique, an initial absorbance reading is first taken of the reagent alone, a sample to be assayed is then added to the reagent, and after equilibrium has been reached a second absorbance reading is taken. From this change in absorbance the phosphorus concentration is calculated.

With the advent of rate analyzers, attempts have been made to produce a rate method for phosphorus determinations. However, to date such attempts have not yielded a rate methodology. In fact, Daly et al (8) reported that "the possibility of an initial rate reaction was eliminated when it was discovered that serum protein had an accelerating effect on the reaction. This phenomena varied from serum to serum without affecting the final absorbance difference between the blank and the reaction product".

Accordingly, it would be very desirable to have a reagent capable of being employed in a rate determination of inorganic phosphorus in serum.

SUMMARY OF THE INVENTION

In accordance with the present invention there is provided a rate method for assaying inorganic phosphorus and a reagent for use therein. The reagent of this invention is of the type comprising an acid, a molybdate salt, a non-ionic surfactant, and polyvinylpyrrolidone (PVP). The reagent of this invention is characterized in that it further comprises an enhancing amount of at least one sugar alcohol.

The present invention also encompasses a method for assaying inorganic phosphorus. This method is of the type which comprises mixing a sample of biological fluid with a reagent and measuring the absorbance of the resulting solution. The method of the present invention is characterized in that the above reagent is employed therein. The method can further be characterized in that the measurement can be made via a rate technique.

Still other features and attendant advantages of the present invention will become apparent to those skilled in the art from a reading of the following detailed description of the preferred embodiments.

DESCRIPTION OF THE PREFERRED EMBODIMENTS

Preferably, the acid is selected from the group consisting of sulfuric acid, nitric acid, hydrochloric acid, citric acid, and mixtures thereof. More preferably the acid is sulfuric acid.

The salt moiety of the molybdate salt is preferably selected from the group consisting of ammonium, sodium, lithium, potassium, and mixtures thereof. More preferably, the salt moiety is ammonium.

Preferably, the non-ionic surfactant is selected from the group consisting of Triton X-100 (polyethylene glycerol-p-isooctylphenyl ether), Brij 35 (polyoxyethylene(23) lauryl ether), Tween 20 (polyoxyethylene(20) sorbitan monolaurate), Tween 80 (polyoxyethylene(20) sorbitan monooleate), and mixtures thereof. More preferably the non-ionic surfactant is Triton X-100 (polyethylene glycerol p-isooctylphenyl ether).

The sugar alcohol is preferably selected from the group consisting of D-mannitol, sorbitol, and mixtures thereof. More preferably, the sugar alcohol is D-mannitol.

The reagent can be prepared via any technique well known to those skilled in the art. It is preferred to employ a defoamer during such reagent preparation. One typical defoamer is butanol. Butanol is preferably employed in an amount of about 0.005 to about 0.5, more preferably about 0.01 to about 0.1, and optimally about 0.015 to about 0.05% (v/v).

The exact concentrations of the various constituents employed in the present reagent are not critical. However, when the reagent is prepared in a working reagent configuration, the various constituents preferably have the concentrations set forth in Table I.

TABLE I

| Constituent | Preferred | More Preferred | Optimum |
|---|---|---|---|
| Molybdate salt, mM | 0.5–10 | 2–5 | 2.5–4 |
| Acid, M | 0.1–2 | 0.2–1 | 0.3–0.7 |
| PVP, % (w/v) | 0.5–8 | 1–6 | 2–5 |
| Non-ionic surfactant, % (w/v) | 0.05–2 | 0.1–0.5 | 0.15–0.3 |
| Sugar alcohol, mM | 5–400 | 20–100 | 40–70 |

For purposes of stability, it is preferred to place the molybdate salt in a first container, the non-ionic surfactant, PVP, and sugar alcohol in a second container, and to distribute the acid in a preselect manner between the first and second containers. The exact concentrations of the various constituents present in this embodiment are also not critical. However, the preferred concentrations of the various constituents in this configuration are set forth in Table II.

TABLE II

| Constituent | Preferred | More Preferred | Optimal |
|---|---|---|---|
| First Container | | | |
| Molybdate salt, mM | 10–100 | 20–40 | 28–36 |
| Acid, M | 0.4–6 | 0.7–1.5 | 0.9–1.1 |
| Second Container | | | |
| PVP, % (w/v) | 0.5–8 | 2–5 | 3.5–4.5 |
| Sugar alcohol, mM | 5–400 | 20–100 | 40–70 |
| Acid, M | 0.1–1 | 0.7–1.5 | 0.4–0.6 |

TABLE II-continued

| Constituent | Preferred | More Preferred | Optimal |
|---|---|---|---|
| Non-ionic surfactant, % (w/v) | 0.05–2 | 0.15–0.5 | 0.2–0.3 |

In one optimal embodiment of the two container configuration of the present invention, the first container comprises 4% (w/v) ammonium molybdate and 1M sulfuric acid and the second container comprises 4% (w/v) PVP, 1% (w/v) D-mannitol, 0.5M sulfuric acid, and 0.25% (w/v) Triton X-100 (polyethylene glycerol p-isooctylphenyl ether).

A working reagent for a rate method can be prepared by mixing one part of the first container with 9 parts of the second container.

The incorporation of mannitol into the reagent slows down the formation rate of phosphomolybdate significantly. As a result, the rate can be monitored conveniently with a rate colorimeter in a 10 to 20 seconds time span. Using 15 µl of sample per 1 ml of reagent, the rate method has an excellent linear range (i.e., linear to 20 mg/dl of phosphorus). The use of mannitol also supresses the effect of serum matrix on the rate. Consequently, the serum assay results of the rate methodology of the present invention correlate very well with those obtained from an end point method.

The following examples are provided for the purpose of further illustration only and are not intended to be limitations on the disclosed invention.

EXAMPLE 1

Reagents having the formulation set forth in Table III were prepared.

TABLE III

| Constituent | Reagent Within Invention | Reagent Outside Invention |
|---|---|---|
| Ammonium Molybdate, mM | 0.32 | 0.32 |
| Sulfuric acid, M | 0.9 | 0.9 |
| PVP, % (w/v) | 3.6 | 3.6 |
| D-mannitol, mM | 22 | 0 |
| Triton X-100 (polyethylene glycerol p-isooctylphenyl ether), % (w/v) | 0.225 | 0.225 |

The reagent within the scope of this invention maintained its linearity for 2 months at room temperature.

The reagent outside the scope of the present invention, which differed solely in the absence of the sugar alcohol, namely D-mannitol, exhibited a 10% reduction in recovery at 17 mg/dl of phosphorus in only 8 days.

As Example 1 indicates, the use of a sugar alcohol in the reagent of the present invention improves the stability of the molybdate solution. It has been found that the usable life of a working reagent containing D-mannitol is approximately 6 times longer than D-mannitol deficient reagent.

Based on this disclosure, many other modifications and ramifications will naturally suggest themselves to those skilled in the art. These are intended to be within the scope of this invention.

BIBLIOGRAPHY

1. Woods, et al., *Ind. Eng. Chem.*, 13: 760 (1941).
2. U.S. Pat. No. 3,795,484.
3. U.S. Pat. No. 3,874,853.
4. U.S. Pat. No. 3,547,586.
5. U.S. Pat. No. 3,425,805.
6. U.S. Pat. No. 3,953,359.
7. U.S. Pat. No. 3,853,469.
8. Daly et al., *Clin. Chem.*, 18: 263 (1972).

The embodiments of the invention in which an exclusive property or privilege is claimed are defined as follows:

1. A rate method for measuring the amount of inorganic phosphate in a sample comprising:
   (a) mixing a sample of biological fluid with a rate reagent comprising an acid, a molybdate salt, a nonionic surfactant, polyvinylpyrrolidone (PVP), and at least one sugar alcohol to produce a mixture; and,
   (b) measuring the rate of formation of phosphomolybdate in the mixture as a measure of the amount of inorganic phosphate in the sample.

2. The rate method of claim 1 wherein:
   (a) said acid is selected from the group consisting of sulfuric acid, nitric acid, hydrochloric acid, citric acid and mixtures thereof;
   (b) said salt is selected from the group consisting of ammonium, sodium, lithium, and potassium salts and mixtures thereof;
   (c) said non-ionic surfactant is selected from the group consisting of Triton X-100 (polyethylene glycerol p-isooctylphenyl ether), Brij 35 (polyxyethylene(23) ether), Tween 20 (polyoxyethylene(20) sorbitan monolaurate), Tween 80 (polyoxyethylene(20) sorbitan monooleate) and mixtures thereof; and
   (d) said sugar alcohol is selected from the group consisting of D-mannitol, sorbitol, and mixtures thereof.

3. The rate method of claim 1 wherein:
   (a) said acid is sulfuric acid;
   (b) said salt is an ammonium salt;
   (c) said non-ionic surfactant is Triton X-100 (polyethylene glycerol p-isooctylphenyl ether); and
   (d) said sugar alcohol is D-mannitol.

4. The rate method of claim 1 wherein said reagent comprises:
   (a) from about 0.5 to about 10 mM ammonium molybdate;
   (b) from about 0.1 to about 2M sulfuric acid;
   (c) from about 0.5 to about 8% (w/v) PVP;
   (d) from about 0.05 to about 2% (w/v) Triton X-100 (polyethylene glycerol p-isooctylphenyl ether); and
   (e) from about 5 to about 400 mM D-mannitol.

5. The rate method of claim 1 wherein said acid is selected from the group consisting of sulfuric acid, nitric acid, hydrochloric acid, citric acid, and mixtures thereof.

6. The rate method of claim 1 wherein said salt is selected from the group consisting of ammonium, sodium, lithium, and potassium salts and mixtures thereof.

7. The rate method of claim 1 wherein said non-ionic surfactant is selected from the group consisting of Triton X-100 (polyethylene glycerol p-isooctylphenyl ether), Brij 35 (polyoxyethylene(23) ether), Tween 20 (polyoxyethylene(20) sorbitan monolaurate), Tween 80 (polyoxyethylene(20) sorbitan monooleate) and mixtures thereof.

8. The rate method of claim 1 wherein said sugar alcohol is selected from the group consisting of D-mannitol, sorbitol, and mixtures thereof.

9. The rate method of claim 1 wherein said acid is sulfuric acid.

10. The rate method of claim 1 wherein said salt is an ammonium salt.

11. The rate method of claim 1 wherein said nonionic surfactant is Triton X-100 (polyethylene glycerol p-isooctylphenyl ether).

12. The rate method of claim 1 wherein said sugar alcohol is D-mannitol.

13. The rate method of claim 1 wherein:
(a) said molybdate salt is initially contained in a first container,
(b) said non-ionic surfactant, said PVP, and said sugar alcohol are initially contained in a second container,
(c) said acid is initially contained in both said first and second containers, and
(d) predetermined portions of the contents of said first and second containers are mixed together to form said rate reagent.

14. The rate method of claim 13 wherein:
(a) said first container contains:
   (i) from about 10 to about 100 mM ammonium molybdate, and
   (ii) from about 0.4 to about 6M sulfuric acid;
(b) said second container contains:
   (i) from about 0.5 to about 8% (w/v) PVP;
   (ii) from about 5 to about 400 mM D-mannitol;
   (iii) from about 0.1 to about 1M sulfuric acid; and
   (iv) from about 0.05 to about 2% (w/v) Triton X-100 (polyethylene glycerol p-isooctylphenyl ether); and
(c) about one part of the contents of said first container is mixed with about 9 parts of the contents of said second container to form said rate reagent.

* * * * *